US008876868B2

(12) United States Patent
Jackson

(10) Patent No.: US 8,876,868 B2
(45) Date of Patent: Nov. 4, 2014

(54) HELICAL GUIDE AND ADVANCEMENT FLANGE WITH RADIALLY LOADED LIP

(76) Inventor: Roger P. Jackson, Prairie Village, KS (US)

(*) Notice: Subject to any disclaimer, the term of this patent is extended or adjusted under 35 U.S.C. 154(b) by 2166 days.

(21) Appl. No.: 11/101,859

(22) Filed: Apr. 8, 2005

(65) Prior Publication Data

US 2005/0182410 A1    Aug. 18, 2005

Related U.S. Application Data

(63) Continuation-in-part of application No. 10/831,919, filed on Apr. 26, 2004, now Pat. No. 8,273,109, which is a continuation-in-part of application No. 10/236,123, filed on Sep. 6, 2002, now Pat. No. 6,726,689.

(60) Provisional application No. 60/627,000, filed on Nov. 10, 2004.

(51) Int. Cl.
| | |
|---|---|
| *A61B 17/70* | (2006.01) |
| *F16B 35/04* | (2006.01) |
| *F16B 33/02* | (2006.01) |
| *A61B 17/86* | (2006.01) |
| *A61B 19/00* | (2006.01) |

(52) U.S. Cl.
CPC ......... *A61B 17/7037* (2013.01); *A61B 17/7032* (2013.01); *F16B 33/02* (2013.01); *A61B 2017/8655* (2013.01); *A61B 2019/307* (2013.01); *F16B 35/047* (2013.01)
USPC ...................................................... 606/273

(58) Field of Classification Search
USPC ......... 606/246, 264, 265, 266, 267, 270, 272, 606/273, 275, 278, 279, 300, 301, 305, 306, 606/308; 411/2, 3, 5, 393; 403/362
See application file for complete search history.

(56) References Cited

U.S. PATENT DOCUMENTS

| 791,548 A | 6/1905 | Fischer |
|---|---|---|
| 1,300,275 A | 4/1919 | Johnson |

(Continued)

FOREIGN PATENT DOCUMENTS

| DE | 3630863 | 3/1988 |
|---|---|---|
| DE | 373809 | 5/1989 |

(Continued)

OTHER PUBLICATIONS

Translation of Shafer (DE 298 10 798 U1), Schreiber Translations, Inc., May 2010.*

(Continued)

*Primary Examiner* — Pedro Philogene
*Assistant Examiner* — David Comstock
(74) *Attorney, Agent, or Firm* — John C. McMahon

(57) ABSTRACT

A spinal fixation device combines an open-headed anchor member, such as a bone screw or a hook, with a closure member to thereby clamp a spinal fixation rod to the anchor member. The anchor member has spaced apart arms forming a rod receiving channel. The arms have arm extensions or tabs connected to main portions of the arms by weakened regions to enable the tabs to be broken-off or separated after the rod is clamped. The closure member and inner surfaces of the arms and tabs have helical anti-splay guide and advancement interlocking flanges formed thereon which cooperate to prevent splaying the arms and extensions as the closure member is advanced into the rod receiving channel. The flanges have anti-splay contours which can be formed on load flanks or stab flanks of the flanges. The load flanks can be oriented in such a manner as to aid in the anti-splay characteristics of the flanges or to control the proportioning of axial stresses between the flanges.

2 Claims, 11 Drawing Sheets

(56) References Cited

U.S. PATENT DOCUMENTS

| | | |
|---|---|---|
| 1,330,673 A | 2/1920 | Anderson |
| 2,083,092 A | 1/1936 | Richer |
| 2,201,087 A | 5/1940 | Hallowell |
| 2,239,352 A | 4/1941 | Cherry |
| 2,295,314 A | 9/1942 | Whitney |
| 2,537,029 A | 8/1946 | Cambern |
| 2,445,978 A | 7/1948 | Stellin |
| 2,532,815 A | 12/1950 | Kindsvatter |
| 2,553,337 A | 5/1951 | Shafer |
| 2,778,265 A | 1/1957 | Brown |
| 2,969,250 A | 1/1959 | Kull |
| 2,877,681 A | 3/1959 | Brown |
| 2,927,332 A | 3/1960 | Moore |
| 3,143,029 A | 8/1964 | Brown |
| D200,217 S | 2/1965 | Curtiss |
| 3,370,341 A | 2/1968 | Allsop |
| 3,498,174 A | 3/1970 | Schuster et al. |
| 3,584,667 A | 6/1971 | Reiland |
| 3,640,416 A | 2/1972 | Temple |
| 3,812,757 A | 5/1974 | Reiland |
| 3,963,322 A | 6/1976 | Cryctko |
| 4,103,422 A | 8/1978 | Weiss |
| 4,269,246 A | 5/1981 | Larson et al. |
| 4,373,754 A | 2/1983 | Bollfrass et al. |
| 4,492,500 A | 1/1985 | Ewing |
| 4,506,917 A | 3/1985 | Hansen Arne |
| 4,577,448 A | 3/1986 | Howorth |
| 4,600,224 A | 7/1986 | Blose |
| 4,641,636 A | 2/1987 | Cotrel |
| 4,703,954 A | 11/1987 | Ortloff et al. |
| 4,707,001 A | 11/1987 | Johnson |
| 4,763,644 A | 8/1988 | Webb |
| 4,764,068 A | 8/1988 | Crispell |
| 4,790,297 A | 12/1988 | Luque |
| 4,805,602 A | 2/1989 | Puno et al. |
| 4,815,453 A | 3/1989 | Cotrel |
| 4,838,264 A | 6/1989 | Bremer et al. |
| 4,850,775 A | 7/1989 | Lee |
| 4,946,458 A | 8/1990 | Harms et al. |
| 5,005,562 A | 4/1991 | Cotrel |
| 5,022,791 A | 6/1991 | Isler |
| 5,026,373 A | 6/1991 | Ray et al. |
| 5,067,955 A | 11/1991 | Cotrel |
| 5,073,074 A | 12/1991 | Corrigan et al. |
| 5,092,635 A | 3/1992 | DeLange et al. |
| 5,129,388 A | 7/1992 | Vignaud et al. |
| 5,147,360 A | 9/1992 | Dubousset |
| 5,154,719 A | 10/1992 | Cotrel |
| 5,176,483 A | 1/1993 | Baumann et al. |
| 5,207,678 A | 5/1993 | Harms et al. |
| 5,217,497 A | 6/1993 | Mehdian |
| 5,261,907 A | 11/1993 | Vignaud et al. |
| 5,261,912 A | 11/1993 | Frigg |
| 5,275,601 A | 1/1994 | Gogolewski et al. |
| 5,282,707 A | 2/1994 | Palm |
| 5,312,404 A | 5/1994 | Asher et al. |
| 5,321,901 A | 6/1994 | Kelly |
| 5,334,203 A | 8/1994 | Wagner |
| 5,346,493 A | 9/1994 | Stahurski et al. |
| 5,354,299 A | 10/1994 | Coleman |
| 5,358,289 A | 10/1994 | Banker et al. |
| 5,360,431 A | 11/1994 | Puno et al. |
| 5,364,400 A | 11/1994 | Rego, Jr. et al. |
| 5,382,248 A | 1/1995 | Jacobson et al. |
| 5,385,583 A | 1/1995 | Cotrel |
| 5,387,212 A | 2/1995 | Yuan et al. |
| 5,395,371 A | 3/1995 | Miller et al. |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,487,742 A | 1/1996 | Cotrel |
| 5,496,321 A | 3/1996 | Puno et al. |
| 5,499,892 A | 3/1996 | Reed |
| 5,507,747 A | 4/1996 | Yuan et al. |
| 5,545,165 A | 8/1996 | Biedermann et al. |
| 5,554,157 A | 9/1996 | Errico et al. |
| 5,562,663 A | 10/1996 | Wisnewski et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,591,235 A | 1/1997 | Kuslich |
| 5,601,553 A | 2/1997 | Trebing et al. |
| 5,607,304 A | 3/1997 | Bailey et al. |
| 5,607,426 A | 3/1997 | Ralph et al. |
| 5,624,442 A | 4/1997 | Mellinger et al. |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,653,710 A | 8/1997 | Harle |
| 5,662,652 A | 9/1997 | Schafer et al. |
| 5,669,911 A | 9/1997 | Errico et al. |
| 5,672,176 A | 9/1997 | Biedermann et al. |
| 5,681,319 A | 10/1997 | Biedermann et al. |
| 5,683,390 A | 11/1997 | Metz-Stavenhagen et al. |
| 5,690,630 A | 11/1997 | Errico et al. |
| 5,697,929 A | 12/1997 | Mellinger |
| 5,713,705 A | 2/1998 | Grunbichler |
| 5,713,898 A | 2/1998 | Stucker et al. |
| 5,716,356 A | 2/1998 | Biedermann et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,782,833 A | 7/1998 | Haider |
| 5,797,911 A | 8/1998 | Sherman |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| D407,302 S | 3/1999 | Lawson |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,902,303 A | 5/1999 | Eckhof et al. |
| 5,944,465 A | 8/1999 | Janitzki |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,078 A | 4/2000 | Parker |
| 6,053,917 A | 4/2000 | Sherman et al. |
| 6,056,753 A | 5/2000 | Jackson |
| 6,059,786 A | 5/2000 | Jackson |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,139,550 A * | 10/2000 | Michelson ............ 606/70 |

(56) References Cited

U.S. PATENT DOCUMENTS

| | | |
|---|---|---|
| 6,143,032 A | 11/2000 | Schafer et al. |
| 6,146,383 A | 11/2000 | Studer et al. |
| 6,149,533 A | 11/2000 | Finn |
| 6,183,472 B1 | 2/2001 | Lutz |
| 6,187,005 B1 | 2/2001 | Brace et al. |
| 6,193,719 B1 | 2/2001 | Gournay et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,248,105 B1 | 6/2001 | Schlapfer et al. |
| 6,254,146 B1 | 7/2001 | Church |
| 6,254,602 B1 | 7/2001 | Justis |
| 6,261,039 B1 | 7/2001 | Reed |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 * | 10/2001 | Morrison et al. ............. 606/305 |
| 6,302,888 B1 | 10/2001 | Mellinger |
| 6,309,391 B1 | 10/2001 | Crandall et al. |
| 6,315,564 B1 | 11/2001 | Levisman |
| 6,322,108 B1 | 11/2001 | Riesselmann et al. |
| 6,331,179 B1 | 12/2001 | Freid et al. |
| 6,349,794 B2 | 2/2002 | Spencer |
| 6,355,040 B1 | 3/2002 | Richelsoph et al. |
| RE37,665 E | 4/2002 | Ralph et al. |
| 6,368,321 B1 | 4/2002 | Jackson |
| 6,402,752 B2 | 6/2002 | Schäffler-Wachter et al. |
| 6,440,135 B2 | 8/2002 | Orgay et al. |
| 6,440,137 B1 | 8/2002 | Horvath et al. |
| 6,443,953 B1 | 9/2002 | Perra et al. |
| 6,451,021 B1 | 9/2002 | Ralph et al. |
| 6,454,772 B1 | 9/2002 | Jackson |
| 6,471,703 B1 | 10/2002 | Ashman |
| 6,471,705 B1 | 10/2002 | Biedermann et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,520,963 B1 | 2/2003 | McKinley |
| 6,527,804 B1 | 3/2003 | Gauchet et al. |
| 6,530,929 B1 | 3/2003 | Jusis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,602,255 B1 | 8/2003 | Campbell et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schafer |
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,689 B2 | 4/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 * | 5/2004 | Richelsoph ............... 606/60 |
| 6,740,089 B2 | 5/2004 | Haider |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,790,209 B2 | 9/2004 | Beale et al. |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,932,817 B2 | 8/2005 | Baynham et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,974,460 B2 | 12/2005 | Carbone et al. |
| 6,979,334 B2 | 12/2005 | Dalton |
| 6,981,973 B2 | 1/2006 | McKinley |
| RE39,035 E | 3/2006 | Finn et al. |
| 7,018,378 B2 | 3/2006 | Biedermann et al. |
| 7,018,379 B2 | 3/2006 | Drewry et al. |
| 7,306,606 B2 | 12/2007 | Sasing |
| 2001/0001119 A1 | 5/2001 | Lombardo |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133154 A1 | 9/2002 | Saint Martin |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023243 A1 | 1/2003 | Biedermann et al. |
| 2003/0028191 A1 | 2/2003 | Shluzas |
| 2003/0073996 A1 | 4/2003 | Doubler et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0125741 A1 | 7/2003 | Biedermann et al. |
| 2003/0149432 A1 | 8/2003 | Frigg et al. |
| 2003/0163133 A1 | 8/2003 | Altarac et al. |
| 2003/0176862 A1 | 9/2003 | Taylor et al. |
| 2003/0199873 A1 | 10/2003 | Richelsoph |
| 2003/0208204 A1 | 11/2003 | Bailey et al. |
| 2003/0216735 A1 | 11/2003 | Altarac et al. |

(56) References Cited

U.S. PATENT DOCUMENTS

| | | |
|---|---|---|
| 2004/0006342 A1 | 1/2004 | Altarac et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147929 A1 | 7/2004 | Biedermann et al. |
| 2004/0158247 A1 | 8/2004 | Sitiso et al. |
| 2004/0162560 A1 | 8/2004 | Raynor et al. |
| 2004/0172022 A1 | 9/2004 | Landry et al. |
| 2004/0172032 A1 | 9/2004 | Jackson |
| 2004/0176766 A1 | 9/2004 | Shluzas |
| 2004/0186473 A1 | 9/2004 | Cournoyer et al. |
| 2004/0193160 A1 | 9/2004 | Richelsoph |
| 2004/0210216 A1 | 10/2004 | Farris et al. |
| 2004/0225289 A1 | 11/2004 | Biedermann et al. |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0027296 A1 | 2/2005 | Thramann et al. |
| 2005/0049589 A1 | 3/2005 | Jackson |
| 2005/0055026 A1 | 3/2005 | Biedermann et al. |
| 2005/0070899 A1 | 3/2005 | Doubler et al. |
| 2005/0080415 A1 | 4/2005 | Keyer et al. |
| 2005/0096653 A1 | 5/2005 | Doubler |
| 2005/0107788 A1 | 5/2005 | Beaurain et al. |
| 2005/0113927 A1 | 5/2005 | Malek |
| 2005/0131404 A1 | 6/2005 | Mazda et al. |
| 2005/0131413 A1 | 6/2005 | O'Driscoll et al. |
| 2005/0149023 A1 | 7/2005 | Ritland |
| 2005/0154389 A1 | 7/2005 | Selover et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203516 A1 | 9/2005 | Biedermann et al. |
| 2005/0216003 A1 | 9/2005 | Biedermann et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0240181 A1 | 10/2005 | Boomer et al. |
| 2005/0240183 A1 | 10/2005 | Vaughan |
| 2005/0251137 A1 | 11/2005 | Ball |
| 2005/0251141 A1 | 11/2005 | Frigg et al. |
| 2005/0261687 A1 | 11/2005 | Garamszegi et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277925 A1 | 12/2005 | Mujwid |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0288669 A1 | 12/2005 | Abdou |
| 2005/0288671 A1 | 12/2005 | Yuan et al. |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009769 A1 | 1/2006 | Lieberman |
| 2006/0009770 A1 | 1/2006 | Speirs et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036242 A1 | 2/2006 | Nilsson et al. |
| 2006/0036252 A1 | 2/2006 | Baynham et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |

FOREIGN PATENT DOCUMENTS

| | | |
|---|---|---|
| DE | 9202745.8 | 4/1992 |
| DE | 4425392 | 11/1995 |
| DE | 19507141 | 9/1996 |
| DE | 19509331 | 9/1996 |
| DE | 28910798 | 12/1999 |
| DE | 29810798 | 12/1999 |
| DE | 19951145 | 5/2001 |
| DE | 10157969 | 2/2003 |
| EP | 195455 | 9/1986 |
| EP | 172130 | 2/1987 |
| EP | 276153 | 7/1988 |
| EP | 0276153 | 7/1988 |
| EP | 465158 | 1/1992 |
| EP | 0885598 | 12/1998 |
| EP | 1090595 | 4/2001 |
| EP | 1121902 | 8/2001 |
| EP | 1190678 | 3/2002 |
| EP | 1210914 | 6/2002 |
| EP | 1277444 | 1/2003 |
| EP | 1449486 | 8/2004 |
| EP | 1570795 | 9/2005 |
| EP | 1579816 | 9/2005 |
| EP | 1634537 | 3/2006 |
| FR | 2467312 | 4/1981 |
| FR | 2729291 | 7/1996 |
| FR | 2796545 | 1/2001 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| GB | 203508 | 9/1923 |
| GB | 2082709 | 3/1982 |
| GB | 2140523 | 11/1984 |
| GB | 2365345 | 2/2002 |
| JP | 9-504727 | 5/1997 |
| SU | 371359 | 2/1993 |
| WO | WO92/03100 | 3/1992 |
| WO | WO 92/03100 | 5/1992 |
| WO | WO94/10927 | 5/1994 |
| WO | WO94/10944 | 5/1994 |
| WO | WO94/26191 | 11/1994 |
| WO | WO 94/26191 | 11/1994 |
| WO | WO95/35067 | 12/1995 |
| WO | WO96/06576 | 3/1996 |
| WO | WO96/28118 | 9/1996 |
| WO | WO97/14366 | 4/1997 |
| WO | WO98/32386 | 7/1998 |
| WO | WO01/49191 | 7/2001 |
| WO | WO02/054966 | 7/2002 |
| WO | WO03/068088 | 8/2003 |
| WO | WO2004/021900 | 3/2004 |
| WO | WO2004/041100 | 5/2004 |
| WO | WO2004/089245 | 10/2004 |
| WO | WO2004/107997 | 12/2004 |
| WO | WO2005/000136 | 1/2005 |
| WO | WO2005/000137 | 1/2005 |
| WO | WO2005/020829 | 3/2005 |
| WO | WO2005/072632 | 8/2005 |
| WO | WO2005/082262 | 9/2005 |
| WO | WO2005/099400 | 10/2005 |
| WO | WO2006/012088 | 2/2006 |
| WO | WO2006/017616 | 2/2006 |
| WO | WO2006/028537 | 3/2006 |

OTHER PUBLICATIONS

*Spine*, Lipcott, Williams & Wilkins, Inc. vol. 24, No. 15, p. 1495, Aug. 1, 1999.

(56) References Cited

OTHER PUBLICATIONS

Brochure of Tyco/Healthcare/Surgical Dynamics on Spiral Radius 90D, Publication Date: Sep. 2001, pp. 1-8.
Brochure of Tyco/Healthcare/Surgical Dynamks on Spiral Radius 90D, Publication Date: Sep. 2001, pp. 1-8.
CD Horizon M8 Multi Axial Screw Spinal System Brochure, Medtronic Sofamor Danek, no publish date.
EBI Omega 21 Brochure, EBI Spine Systems, pub. 1999.
SDRS Surgical Dynamics Rod System Brochure, Surgical Dynamics, pub. 1998-1999.
Silhouette Spinal Fixation System Brochure, Sulzer Medica Spine-Tech, no publish date.
Spine, Lipcott, Williams & Wilkins, Inc. vol. 24, No. 15, p. 1495.
The Moss Miami 6.0mm System Advertisement, author unknown, no publish date.
The Rod Plate System Brochure, Stryker Howmedica Osteonics, pub. Oct. 1999.
The Strength of Innovation Advertisement, Blackstone Medical Inc., no publish date.
Versalok Low Back Fixation System Brochure, Wright Medical Technology, Inc., pub. 1997.
VLS System Variable Locking Screw Brochure, Interpore Cross International, 1999.
Xia Spinal System Brochure, Stryker Howmedica Osteonics, no publish date.

\* cited by examiner

HELICAL GUIDE AND ADVANCEMENT FLANGE WITH RADIALLY LOADED LIP

CROSS-REFERENCE TO RELATED APPLICATIONS

This application claims the benefit of U.S. Provisional Application No. 60/627,000 filed Nov. 10, 2004 and is a continuation-in-part of U.S. patent application, Ser. No. 10/831,919 filed Apr. 26, 2004 now U.S. Pat. No. 8,273,109, which is a continuation-in-part of U.S. patent application Ser. No. 10/236,123 for HELICAL WOUND MECHANICALLY INTERLOCKING MATING GUIDE AND ADVANCEMENT STRUCTURE filed Sep. 6, 2002, now U.S. Pat. No. 6,726,689, which is incorporated herein by reference.

BACKGROUND OF THE INVENTION

The present invention relates to improvements in interlocking or interconnecting helical guide and advancement structures such as helical flanges and, more particularly, to mating helical flange arrangements having an anti-splay lip on one flange and a cooperating and interlocking anti-splay groove on the other flange, the flanges being configured so that when radial loading or engagement occurs, the lip and groove resist splaying of an outer one of the members having one of the cooperating flanges on it. Such flanges with anti-splay contours are particularly advantageous when used in combination with open headed bone screws formed with extended arms or tabs to facilitate the capture and reduction of spinal fixation rods, after which the arm extensions or tabs are broken off at weakened areas to from a low profile implant. In the present invention, the interlocking anti-splay components are also found on the extensions such that force can be applied to a closure and through the closure to a rod positioned between the extensions without splaying the extensions, since the closure holds them in fixed position relative to each other as the closure traverses between the extensions.

Medical implants present a number of problems to both surgeons installing implants and to engineers designing them. It is always desirable to have an implant that is strong and unlikely to fail or break during usage. Further, if one of a set of cooperating components is likely to fail during an implant procedure, it is desirable to control which particular component fails and the manner in which it fails, to avoid injury and to minimize surgery to replace or repair the failed component. It is also desirable for the implant to be as small and lightweight as possible so that it is less intrusive to the patient. These are normally conflicting goals, and often difficult to resolve.

One type of implant presents special problems. In particular, spinal anchors such as monoaxial and polyaxial bone screws, hooks, and the like are used in many types of back surgery for repair of problems and deformities of the spine due to injury, developmental abnormalities, disease or congenital defects. For example, spinal bone screws typically have one end that threads into a vertebra and a head at an opposite end. The head is formed with an opening to receive a rod or rod-like member which is then both captured in the channel and locked in the head to prevent relative movement between the various elements subsequent to installation.

A particularly useful type of head for such above referenced bone screws is an open head wherein an open, generally U-shaped channel is formed in the head, and the rod is simply laid in the open channel. The channel is then closed with some type of a closure member which engages the walls or arms forming the head and clamps the rod in place within the channel. While the open headed devices are often necessary and preferred for usage, there is a significant problem associated with them. The open headed devices conventionally have two upstanding arms that are on opposite sides of the channel that receives the rod member. The top of the channel is closed by a closure member after the rod member is placed in the channel. Many open headed implants are closed by plugs that screw into threads formed on internal surfaces between the arms, because such configurations have low profiles.

However, such threaded plugs have encountered problems in that they produce radially outward forces that lead to splaying of the arms or at least do not prevent splaying that in turn may lead to loosening of parts and failure of the implant. In order to lock the rod member in place, a significant force must be exerted on the relatively small plug or on a set screw of some type. The forces are required to provide enough torque to insure that the rod member is clamped or locked securely in place relative to the bone screw, so that the rod does not move axially or rotationally therein. This typically requires torques on the order of 100 to 125 inch-pounds.

Because open headed implants such as bone screws, hooks and the like are relatively small, the arms that extend upwardly at the head can be spread by radially outwardly directed forces in response to the application of the substantial torquing force required to clamp the rod member. Historically, early closures were simple plugs that were threaded with V-shaped threads and which screwed into mating threads on the inside of each of the arms. The outward flexure of the arms of the head is caused by mutual camming action of the V-shaped threads of the plug and head as advancement of the plug is resisted by clamping engagement with the rod while rotational urging of the plug continues. If the arms are sufficiently spread, they can allow the threads to loosen, slip, or even disengage and the closure to fail. To counter this, various engineering techniques were applied to the head to increase its resistance to the spreading force. For example, the arms were significantly strengthened by increasing the width of the arms by many times. This is undesirable since it leads to a larger profile implant which is always undesirable and may limit the working space available to the surgeon during implant procedures. Alternatively, external caps were devised which engaged external surfaces of the head. In either case, the unfortunate effect was to substantially increase the bulk, size, and profile of the implant, especially when external nuts are used which may take up so much space along the rod as to leave too little space for all the implants needed.

The radial expansion problem of V-threads has been recognized in various other applications of threaded joints. To overcome this problem, so-called "buttress" threadforms were developed. In a buttress thread, the trailing or thrust surface, also known as the load flank, is oriented perpendicular to the thread axis, while the leading or clearance surface, also known as the stab flank, remains angled. This results in a neutral radial reaction of a threaded receptacle to torque on the threaded member received. However, even buttress threaded closures may fail since they do not structurally resist splaying of the arms. The same is true for square threads that are sometimes used on closures of open headed implants.

Development of threadforms proceeded by applicant from buttress and square threadforms, which have a neutral radial effect on the screw receptacle, to reverse angled threadforms which can positively draw the threads of the receptacle radially inward toward the thread axis when the plug is torqued. In a reverse angle threadform, the trailing side of the external thread is angled toward the thread axis instead of away from the thread axis, as in conventional V-threads and provide an interference fit. However, outward radial forces on the arms at higher torques can lead to slipping from an interference fit. A positive mechanically interlocking structure between the arms and the closure is more desirable and structurally secure. In the present invention, such positive interlocking is also provided in vertical extensions of the arms that are eventually broken away and removed.

When rods are used in spinal fixation systems, it is often necessary to shape the rod in various ways to properly position vertebrae into which open headed bone screws have been implanted. The bone screw or implant heads are minimized in length and height to thereby minimize the impact of the implanted system on the patient. However, it is often difficult to capture a portion of a straight or curved rod in a short implant head to clamp it within the arms. The extensions allow the arms to extend upwardly and capture the rod therebetween. In this way, the closure can be more easily inserted and rotated to drive the rod downwardly into the head of the implant and reduce or realign a vertebra up to the rod.

SUMMARY OF THE INVENTION

The present invention provides improved mating guide and advancement flange interlocking structure for guiding and advancing an inner member into an outer member in response to relative rotation of the inner to the outer member. The structure includes an inner flange on the inner member and an outer flange on the outer member which have complementary contours cooperating on engagement to helically guide the inner member into the outer member by relative rotation about a helical axis and which radially interlock with the opposite structure as the closure is rotated. The inner flange has a radially outward crest and a radially inward root. Conversely, the outer flange has a radially inward crest and a radially outward root.

Each of the inner and outer flange has a respective stab flank on a leading side relative the direction of advancement of the inner member into the outer member and a respective load flank on the trailing side of the flange. At least one of the flanks on one member has anti-splay contours forming a lip or bead which projects axially and extends helically therealong while a corresponding one of the flanks has anti-splay contours forming a complementary groove depressed in an axial direction and positioned to receive the lip. For example, if the lip is formed on the load flank of the inner member at its radial crest, the corresponding groove is formed into the load flank of the outer member near its root.

The lip and groove have radially oppositely facing anti-splay surfaces which are positioned to enable radial engagement or loading of the anti-splay surfaces to resist or prevent splaying of the outer member when the inner member is strongly torqued into the outer member. Preferably, while the anti-splay surfaces on the inner member are continuous, the outer member is divided into two parts which are spaced from one another, and the anti-splay surfaces thereon are discontinuous but helically aligned.

In a first embodiment of the flange, a lip is formed on the load flank of the inner flange adjacent a crest of the flange. The lip has an anti-splay surface or shoulder which faces inwardly toward coincident helical axes of the inner and outer members which form a joint axis common to both members when so engaged. A corresponding groove is formed into the load flank of the outer flange near the root of the outer flange. The groove has an anti-splay surface or shoulder which faces outwardly away from the joint axis of the members. The anti-splay surfaces of the lip and groove are positioned to mutually engage in a radial direction to resist splaying of the outer member when the inner member is strongly torqued into the outer member.

In the first embodiment, the load flanks of the inner and outer flanges are angled in a slightly "positive" direction; that is, in cross section the load flanks form slightly obtuse angles with the joint axis of the members. Alternatively, the load flanks could be substantially perpendicular to the joint axis or slightly "negative"; that is, with the load flanks forming slightly acute angles with the joint axis. Load flanks oriented at a positive angle tend to cause the outer flange to expand when the inner member is advanced into the outer member and strongly torqued. Such expansion can be used to cause the anti-splay surfaces to positively engage. Conversely, a negative angle of the load flanks provides some resistance to expansion tendencies of the outer member at high torque levels and tends to draw the outer flange toward the helical axis. A substantially perpendicular orientation of the load flanks to the joint axis, similar to the load flanks of a buttress or square thread, causes the inner flange to have a substantially neutral radial effect on the outer flange when the inner member is strongly torqued within the outer member. At extremely high levels of torque, it has been found that there is an outward splaying tendency in virtually all orientations of the load flanks.

Assuming that the inner and outer flanges have relatively equal cross sections with generally similar shapes, the outer flange tends to be somewhat stronger than the inner flange. As a result of this, when the inner member is very strongly torqued into the outer member, the inner flange is likely to fail before the outer flange.

The load flanks of the inner and outer flanges can be parallel, outwardly diverging, or outwardly converging. Generally, if the load flanks diverge outwardly, contact between the load flanks occurs near the root of the inner flange and the crest of the outer flange. Such radially inward contact tends to stress the outer flange, in an axial direction, more than the inner flange when the inner member is very strongly torqued in the outer member, since the effective moment arm of contact from the respective root is relatively short for the inner flange and relatively long for the outer flange. Conversely, if the load flanks converge outwardly, the area of contact is spaced a greater distance from the root of the inner flange and a lesser distance from the root of the outer flange. Thus, for outwardly converging load flanks, greater stress is applied to the inner flange. With parallel load flanks, the axial stresses are distributed relatively evenly along the load flanks, such that the inner and outer flanges are stressed relatively evenly. Thus, the proportioning of stresses between the inner and outer flanges can be controlled to some degree by the relative angles of the load flanks of the inner and outer flanges.

Although the preceding description of the load flanges describes the load flank of the inner flange as having a lip and the load flank of the outer flange as having a groove, each load flank could be accurately described as having both a lip and a groove. The lip of the inner flange is defined by a radially inward groove while the groove formed in the outer flange defines a radially inward lip. In any case, the lip of one flange enters the groove of the other flange so that the anti-splay surfaces of the flanges are placed in mutually facing relation when the inner member is advanced into the outer member.

The present invention does not limit the anti-splay contours solely to the load flanks of the inner and outer flanges. There are advantages to be gained by forming the lips and grooves on the respective stab flanks of the inner and outer flanges, on leading sides of the flanges as the inner member is advanced into the outer member. When the inner member is strongly torqued into the outer member, some axial flexure or deformation of the flanges can occur. The flexure results from strong axial loading of the load flanks against one another and is directed away from the load flanks and toward the direction of advancement of the inner member into the outer member. With the anti-splay contours formed on the stab flanks, such flexure tends to force the lip of the inner flange deeper into the groove of the outer flange, thereby reducing any tendency of the lip and groove to slip past one another under high levels of torque.

The present invention also contemplates providing an anti-splay lip on both the load flank and the stab flank of the inner flange and, similarly, an anti-splay groove on both the load flank and the stab flank of the outer flange. Such double sided anti-splay contours benefit from the advantages of both anti-splay contours formed on the load flanks and anti-splay contours provided on the stab flanks of the inner and outer flanges, while providing increased resistance to slippage of the flanges past one another in response to high levels of torque. Additionally, the increased axial dimension of the crest regions of both the inner and outer flanges makes cross engagement or mutual stripping of the flanges virtually impossible.

Although it is desirable to form the arms of an open-headed bone screw and related implants as short as possible to result in a low profile implant, it is often difficult to urge a spinal fixation rod into the U-shaped channel between the arms of such a bone screw head. In general, the rods are shaped to determine the shaped of the corrected curvature of the spinal column and are anchored along their length to open-headed bone screws implanted into individual vertebrae. Because of the complex curvature that must be applied to the rods, it is sometimes difficult to reduce a portion of such a rod toward a selected bone screw or implant in a vertebra with a conventionally formed open-head with spaced arms for receiving both the rod and a closure.

The present invention solves this problem by forming arm extensions or tabs on the screw head which are connected to main portions of the arms by weakened break regions. Inner surfaces of the extensions have the helical guide and advancement flanges formed thereon to receive a closure with a flange complementary to the flange of the arms of the screw head. In particular, the extensions have the same anti-splay structure thereon as is found on the arms and the structure on the extensions is aligned with that on the arms so as to provide a continuous helical path for the mating structure on the closure to follow. The extensions or tabs enable the rod to be captured at a greater distance from the anchoring vertebra and urged toward the vertebra by advancement of the closure toward the open head. When the rod has been seated in the rod receiving channel and in the head sufficiently clamped, the tabs can be broken off the main portions of the arms to provide the desired low profile implant. Just as the anti-splay guide and advancement structure on the closure and arms cooperate to prevent splaying of the arms, the anti-splay structure on the extensions engages with the cooperating anti-splay structure on the closure to prevent unwanted splaying of the extension and guides the closure to allow mating with the guide and advancement structure on the arms simply by rotating the closure. That is, the guide and advancement structure on the closure does not have to be realigned with the cooperating structure on the arms, and pressure applied to the rod while between the extensions is continued as the rod passes between the arms.

The anti-splay lip and groove of the flanges of the present invention make the use of such extended arms or tabs possible, even when substantial force must be applied to the rod. This is a substantial improvement over use of V-threads, as well as buttress, square, and reverse angle threads that may cause outward splaying of the extensions as force is applied to the rod by the closure.

OBJECTS AND ADVANTAGES OF THE INVENTION

The principal objects of the present invention include: providing an improved helical guide and advancement flange structure for guiding and advancing an inner member into an outer member; providing, particularly, improvements in helical guide and advancement flanges incorporating radially loaded lip and groove contours; providing such flange structure wherein the outer member is subject to being splayed in reaction to advancement and strong torquing of the inner member within the outer member and wherein an inner flange of the inner member and an outer flange of the outer member are particularly configured to cooperate in such a manner as to resist such splaying; providing such flange structure in which the inner and outer flanges are provided with contours including mutually facing surfaces which radially engage when the inner member is advanced into the outer member to resist splaying of the outer member; providing such flange structure in which anti-splay contours are formed on a trailing load flank of each flange to form an anti-splay lip near a crest region of the inner flange and a cooperating anti-splay groove near a root region of the outer flange; providing such flange structure in which the anti-splay contours are alternatively applied to a leading stab flank of each flange to form an anti-splay lip near a crest region of the inner flange and a cooperating anti-splay groove near a root region of the outer flange; providing such flange structure in which the anti-splay contours are alternatively formed on both the load and stab flanks of each flange to form anti-splay lips near a crest region of the inner flange and cooperating anti-splay grooves near a root region of the outer flange; providing such flange structure in which proportioning of mutual axial stresses on the engaged flanged can be controlled by selectively adapting the mutual angles of the engaged load flanks relative to a helical axis in such a manner as to control the region of engagement of the load flanks, with parallel load flanks distributing the axial stresses evenly along the flanks, with converging flanks applying a greater proportion of the axial stresses on the inner flange, and diverging flanks applying a greater proportion of the axial stresses to the outer flange; providing alternative embodiments of such flange structure in which the load flanks of the flanges can be angled positively with respect to the helical axis to positively engage the anti-splay surfaces of the flanges, angled negatively relative to the helical axis so that engagement of the load flanks contributes additional resistance to splaying of the outer member, or angled substantially perpendicular to the helical axis to have a neutral effect on the anti-splay properties of the flanges; providing such flange structure which is particularly well adapted for use in surgically implanted structure, such as spinal fixation hardware and, particularly, to receivers and cooperating closure plugs which are used to receive and clamp spinal fixation rods; providing such flange structure which is particularly well adapted for use with open headed bone screws which have extended arms for facilitating the capture and reduction of spinal fixation rods and which are afterwards separated from the screw heads to provide low profile implants; and providing such improved helical guide and advancement flanges with radially loaded lips which are economical to manufacture, which are strong and effective in use, and which are particularly well adapted for their intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
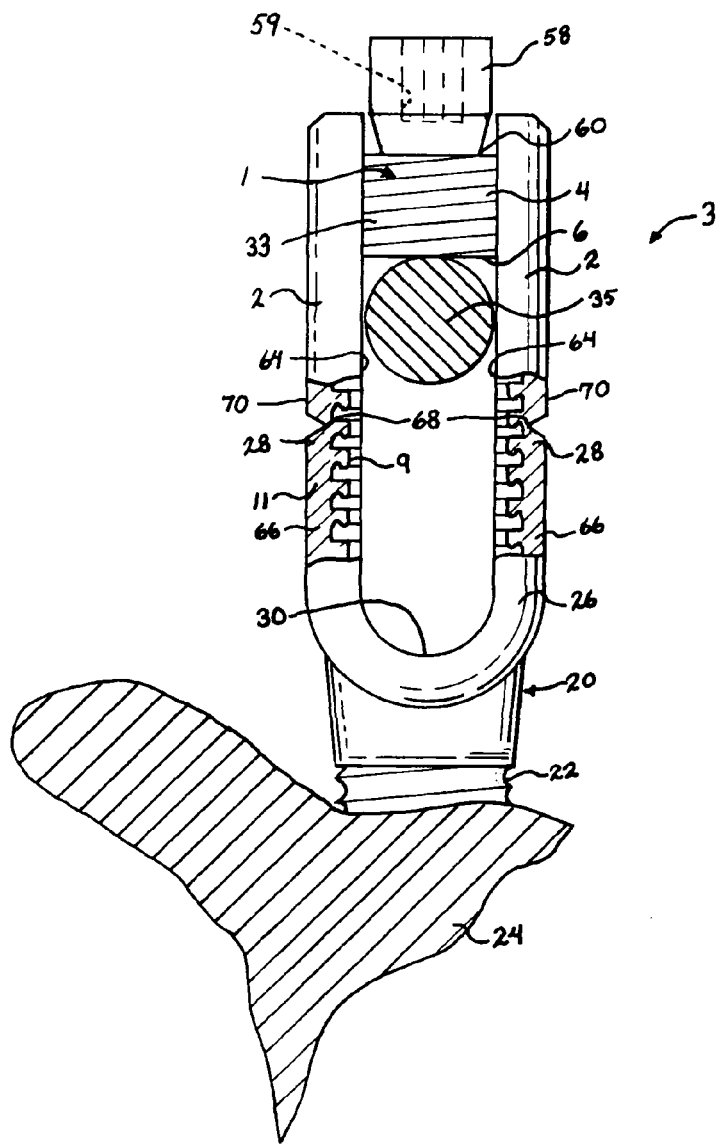
FIG. 1 is an enlarged fragmentary side elevational view of a spinal implant incorporating the helical guide and advancement flange with a radially loaded lip which embodies the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally designates a helical guide and advancement flange structure with radially loaded lips and grooves incorporated in a medical implant 3 and embodying the present invention. The implant 3 can be of a fixed or monoaxial nature or, alternatively, it can have a polyaxial mechanism. The flange structure, or flange form, 1 generally includes an inner flange 4 (FIG. 3) extending helically on an inner member 6 and an outer flange 9 extending helically within an outer member 11. The flanges 4 and 9 cooperate to helically guide the inner member 6 into the outer member 11 when the inner member 6 is rotated and advanced into the outer member 11. The inner and outer flanges 4 and 9 have respective anti-splay contours 14 and 16 which cooperate to prevent splaying tendencies of the outer member 11 when the inner member 6 is strongly torqued therein.

In the illustrated embodiment, the implant 3 includes an open-headed bone screw 20 forming the outer member 11 and having a threaded shank 22 adapted for threaded implanting into a bone, such as a vertebra 24. The screw 20 has a U-shaped open head 26 formed by spaced apart arms 28 defining a rod receiving channel 30 which is configured to receive a rod 35 therein to clamp the rod within the head 26 to thereby fix the position of the vertebra 24 relative to the rod 35 or other vertebrae.

The illustrated inner member 6 is a closure plug or closure 33 which is helically advanced by rotation into the head 26 of the screw 20 and torqued against the rod 35 to clamp the rod within the head 26. Although embodiments of the outer member 11 and inner member 6 are illustrated herein as the screw head 26 and the closure 33, the flange structure 1 is not intended to be limited to such an application. The implant 3 could alternatively be a hook, connector, or other type of implant structure having a rod receiving channel. Also, while the illustrated screw 20 is shown as a fixed one-piece or monoaxial screw, it is intended that the flange structure 1 be adaptable for use with a polyaxial type of screw.

The inner flange 4 has a load flank 39 on a trailing side relative to a direction of advancement along a helical axis 41 (FIG. 3) and a stab flank 43 on an opposite leading side. Similarly, the outer flange 9 has a load flank 46 on a trailing side and a stab flank 48 on an opposite leading side. The load flanks 39 and 46 may also be referred to as thrust surfaces of the flanges 4 and 6, while the stab flanks 42 and 48 may also be referred to as clearance surfaces. In general, the load flanks 39 and 46 are positively engaged and axially loaded, that is loaded in the direction of the axis 41, when the inner member 4 is advanced into the inner member 6. As relative torque between the inner member 4 and the outer member 6 increases, by engagement with a clamped member such as the rod 35, there is a tendency for the arms 28 of the outer member 11 to splay outward, away from the axis 41. In the flange structure 1 of the present invention, the inner and outer anti-splay contours 14 and 16 include respective anti-splay surfaces 52 and 54 which are mutually engaged in a radial direction to resist such splaying tendencies. Because of the anti-splay configuration of the flange structure 1, the relative torque between the inner and outer members 4 and 6 can be much higher than with conventional V-threads or with guide and advancement structures which do not have anti-splay contours, thereby resulting in a considerably higher, more positive and more secure clamping force applied to the rod 35 by a more highly torqued closure member 33.

Figure 3:
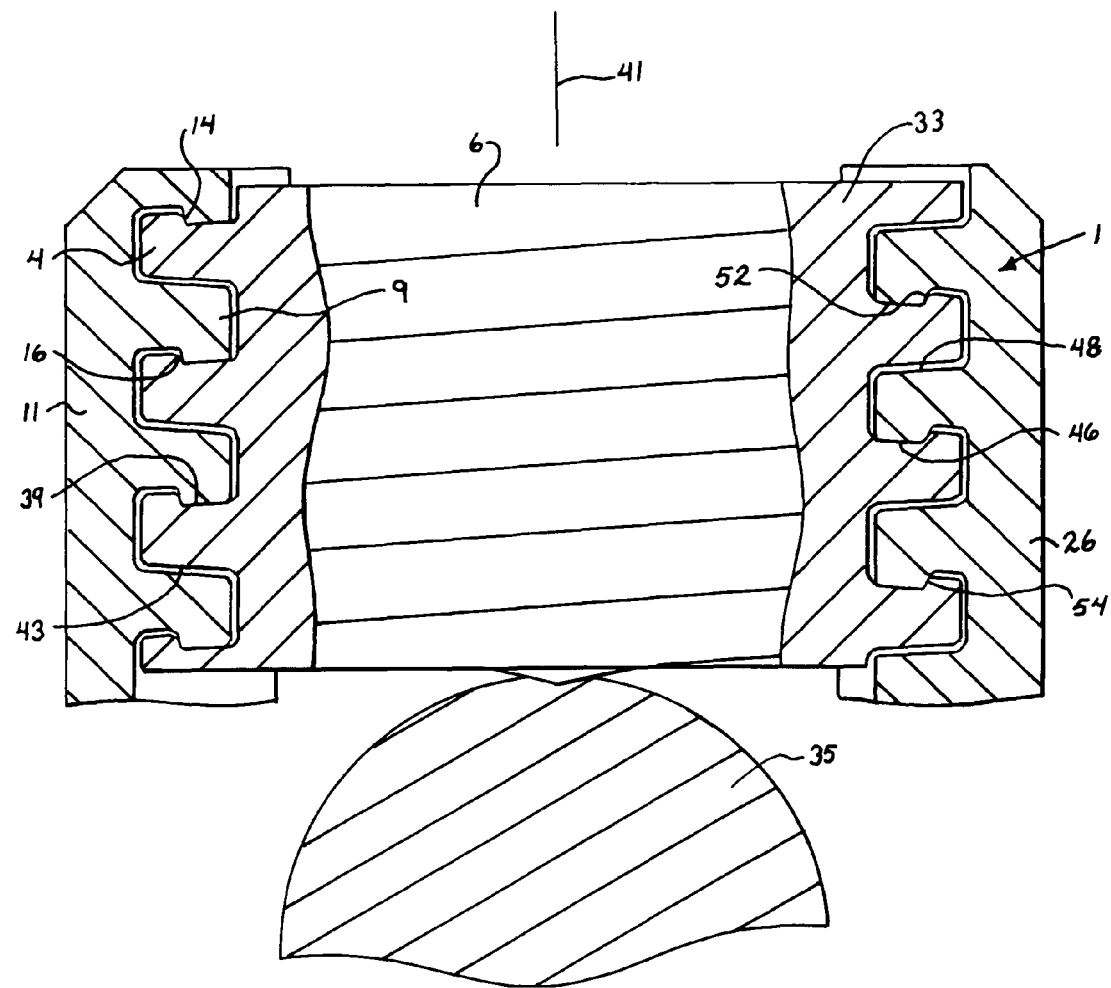
FIG. 3 is a greatly enlarged fragmentary sectional view at a right angle to the view shown in FIG. 2 and illustrates details of the cooperating flanges with the closure strongly torqued into the open headed screw.
Figure 4:
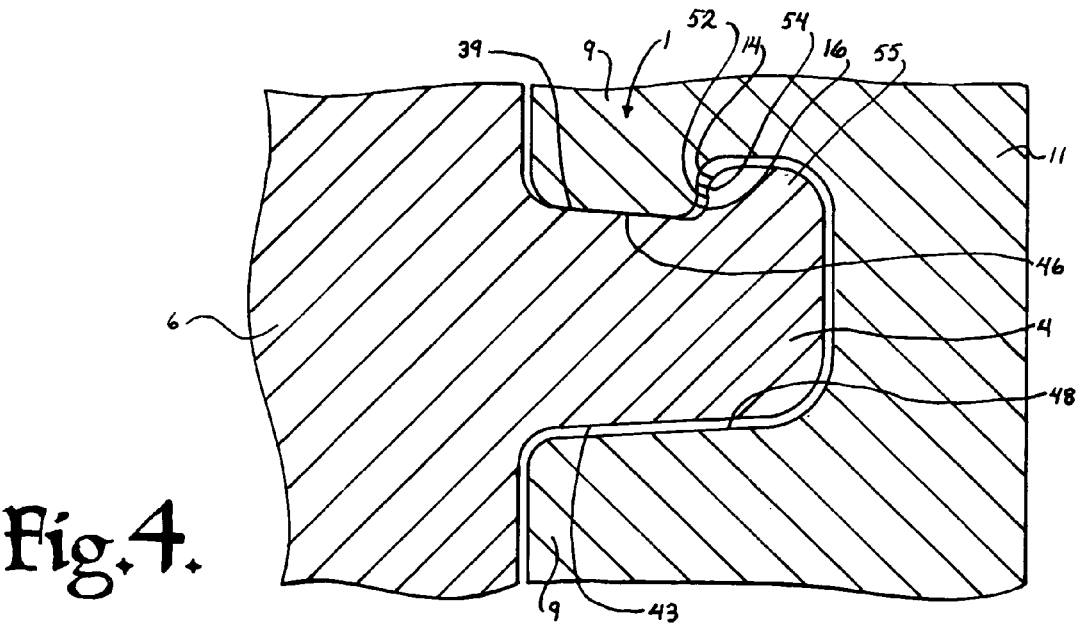
FIG. 4 is a further enlarged fragmentary sectional view of a preferred flange structure according to the present invention and illustrates an anti-splay lip on a load flank of an inner flange and an anti-splay groove on a load flank of an outer flange, the load flanks being parallel and somewhat positive in angular orientation relative to a helical axis.
Figure 5:
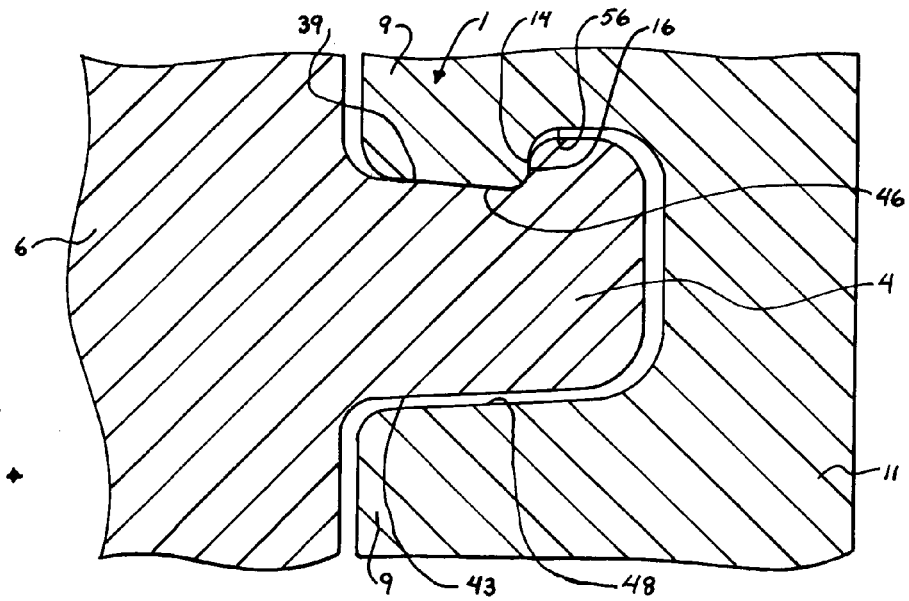
FIG. 5 is a view similar to FIG. 4 and illustrates the preferred flange structure with the inner member strongly torqued within the outer member, thereby mutually engaging the anti-splay surfaces of the lip and groove.

In the illustrated flange structure 1, the inner anti-splay surface 52 is formed by an anti-splay lip 55 extending axially from the load flank 39 of the inner flange 4. Similarly, the outer anti-splay surface 54 is formed by a groove 56 formed into the load flank 46 of the outer flange 9. The lip 55 and groove 56 are shaped in a complementary manner so that the lip 55 is received within the groove 56 when the inner member 6 is advanced into the outer member 11. Although FIGS. 3-5 illustrate a flange structure 1 of a particular configuration and contour, other configurations and contours are contemplated, as disclosed in Ser. No. 10/236,123 referenced above and incorporated herein by reference and as disclosed in FIGS. 6-19 and described below.

The closure 33 illustrated in FIG. 1 has a break-off installation head 58 which is provided with a non-round installation socket 59, such as a Torx shaped socket, a hexagonal Allen socket, or the like to receive an appropriately configured installation tool (not shown). The break-off head 58 is joined to the main body of the closure 33 by a weakened region 60 which is configured to limit the torque that can be applied to the head 58, relative to the closure 33, without the head separating from the closure 33 by failure of the weakened region 60. By this means, the head 58 separates from the closure 33 when a selected torque is reached in clamping the rod 35, to thereby provide a low profile implant. Alternatively, the closure 33 could be provided without the break-off head 58. The closure 33 has a non-round socket 61 (FIG. 2) to receive a tool to enable removal of the closure 33 from the screw head 26, if necessary. Such a socket 61 could also be employed for installation of the closure 33 into the screw head 26.

Referring particularly to FIG. 1, the bone screw 20 is provided with the arm tabs on extensions 2 to increase the initial length of the arms 28 and, thus, forming a rod receiving passageway between the extensions 2 and thereby increasing the length of the rod receiving channel 30 by the length of the passageway. The purpose for the lengthened channel 30 is to enable capture of the rod 35 within the channel 30 at a greater distance from the vertebra 24, whereby the rod 35 can be captured by the closure 33 and "reduced" or urged toward a seated position within the channel 30 by advancement of the closure 33. This provides effective leverage in reducing the position of the rod 35 or the vertebra itself. For this purpose, inner surfaces 64 of the tabs 2 are provided with the helical outer flange 9 which extends continuously from main portions 66 of the arms 28 and along the extensions 2 to form a continuous and uniform helical pathway therebetween.

Figure 2:
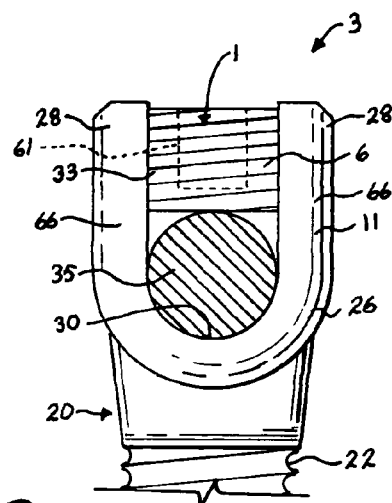
FIG. 2 is a view similar to FIG. 1 and shows the implant with a closure having the flange clamping a spinal fixation rod within an open headed screw head.

The break-off extensions 2 are connected to the main portions 66 of the arms 28 by reduced or otherwise weakened regions 68. The bone screw 20 illustrated in FIG. 1 shows the weakened regions 68 as regions adjacent V-shaped notches formed into external surfaces 70 of the arms 28 which diminish the thickness of the material forming the arms 28. Alternatively, other shapes or configurations could be employed to form the weakened regions 68. The weakened regions 68 are strong enough to enable the rod 35 to be urged toward its seated position (FIG. 2). However, the extensions 2 can be broken off or separated from the main portions 66 of the arms 28 by pivoting or bending the extensions 2 back and forth about the regions 68 while the main portions 66 are held in place, after the closure 33 has passed between the extensions 2. The resulting low-profile implanted structure 3 is shown in FIG. 2.

In addition to resisting splaying of the outer member 11, the configuration of the anti-splay contours 14 and 16 and the general configuration of the inner and outer flanges 4 and 9 can be varied to achieve other beneficial effects in the engagement of the inner and outer members 6 and 11.

Referring FIGS. 3-5, the load flanks 39 and 46 are angled in a slightly "positive" direction. A positive angular direction for the load flanks, as defined herein, is an obtuse angle, that is, an angle of greater than 90 degrees relative to the helical axis 41. A somewhat positive angle is desirable in the load flanks 39 and 46 for relative ease of manufacture of the flange structure 1. A disadvantage of positively angled load flanks 39 and 46 is that there is an outward camming reaction between the engaged load flanks 39 and 46 when the inner and outer members 6 and 11 are strongly torqued, thus causing an outward splaying of the outer member 11, as is shown in FIG. 5. However, engagement of the anti-splay surfaces 52 and 54 limits splaying of the outer member 11.

It should be noted that the inner and outer load flanks 39 and 46 are locally parallel, resulting in relative even distribution of stresses in an axial direction over the surfaces of the load flanks 39 and 46. It should also be noted that a height of the anti-splay lip 55 is slightly less than the depth of the anti-splay groove 56. The result of this is that axial engagement between the inner and outer flanges 4 and 9 is restricted to the load flanks 39 and 46 and does not occur between a peak surface of the lip 55 and a trough surface of the groove 56. It is foreseen that the lip and groove 55 and 56 could alternatively be configured so that axial engagement between the peak of the lip 55 and the trough of the groove 56 could occur.

Figure 6:
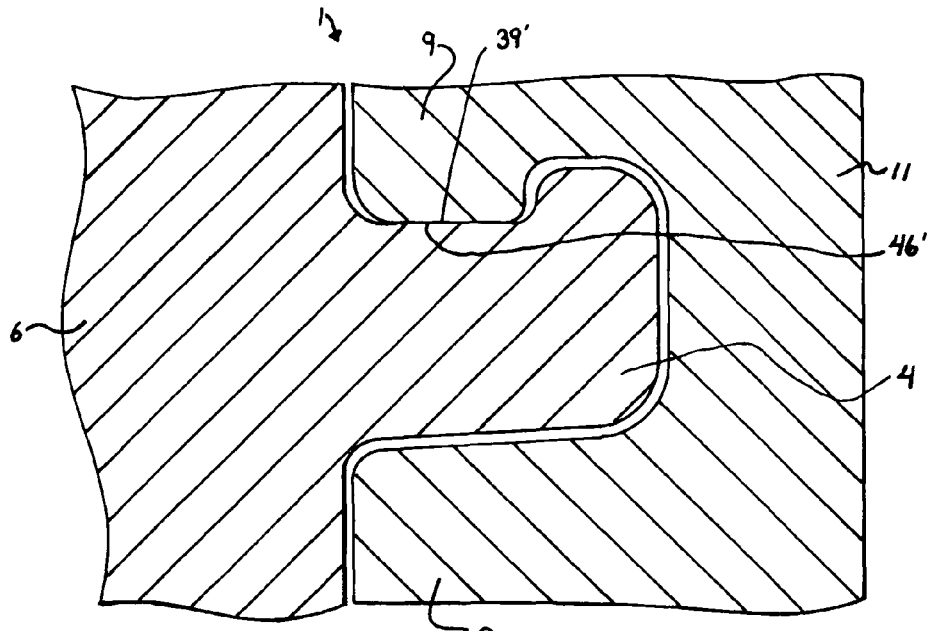
FIG. 6 is a view similar to FIG. 4 and illustrates an alternative embodiment of the flange structure in which the load flanks are parallel and substantially perpendicular to the helical axis.
Figure 7:
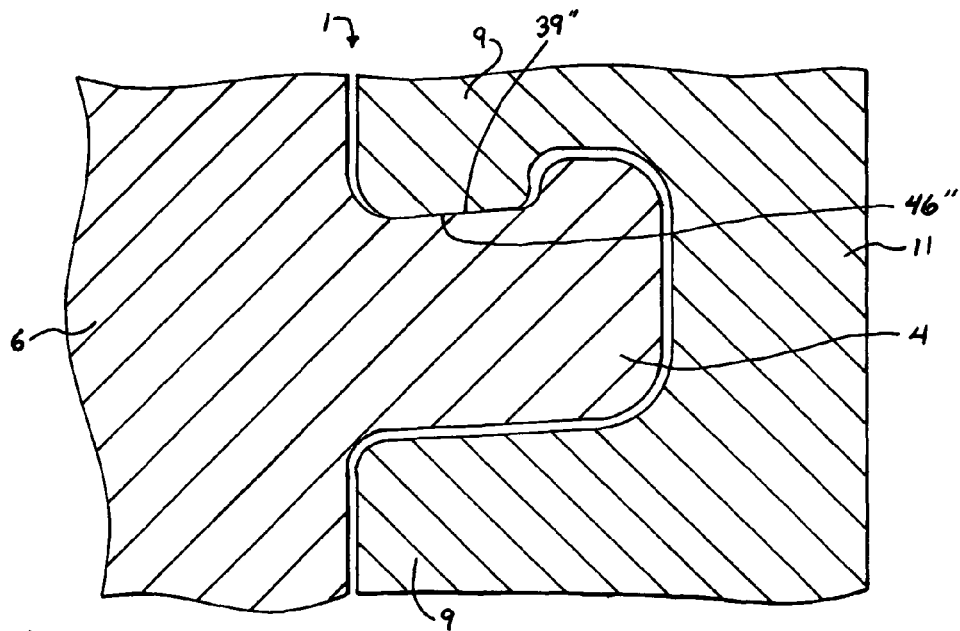
FIG. 7 is a view similar to FIG. 4 and illustrates an alternative embodiment of the flange structure in which the load flanks are parallel and somewhat negative in angular orientation relative to the helical axis.

FIGS. 6 and 7 show alternative configurations of the load flanks 6 and 11. In the embodiment of FIG. 6, inner and outer load flanks 39' and 46' are mutually parallel and perpendicular to the helical axis 41. Perpendicular load flanks have virtually no outward camming reaction to strong torquing of the inner and outer members 6 and 11, resulting in no tendency of the outer member 11 to splay outwardly. In FIG. 7, inner and outer load flanks 39" and 46" are oriented at a slightly negative angle relative to the helical axis 41. A negative angle of a load flank is defined herein as an acute angle or angle of less than 90 degrees relative to the helical axis 41. A negative angling of the load flanks 39" and 46" causes the outer member 11 to be drawn toward the helical axis 41 when the inner and outer members 6 and 11 are strongly torqued, by camming action of the load flanks 39" and 46". The load flanks 39" and 46" are mutually parallel so that axial stresses between the inner and outer flanges 4 and 9 is distributed relatively evenly over the surfaces of the load flanks 39" and 46".

Figure 8:
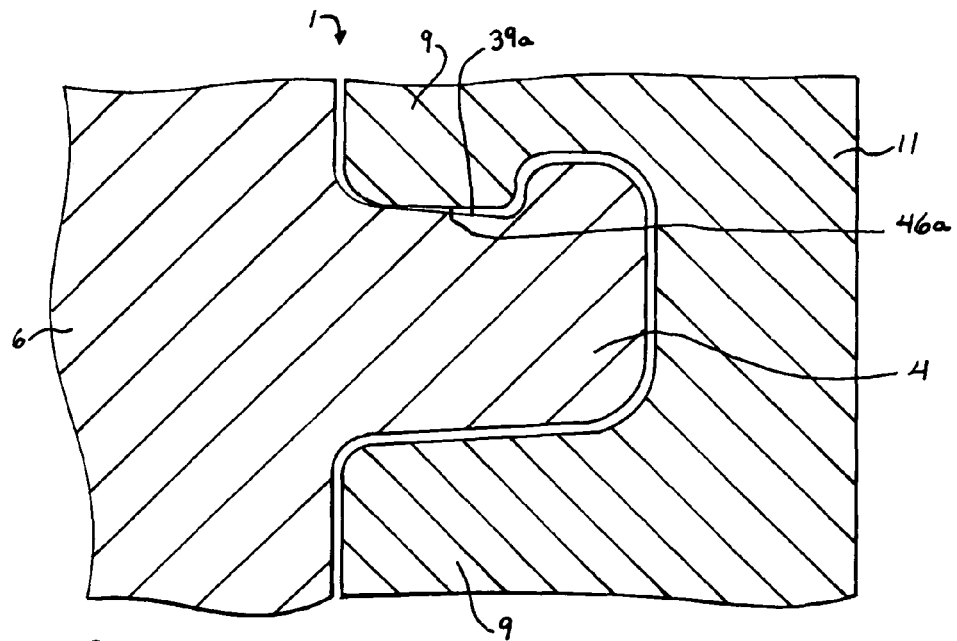
FIG. 8 is a view similar to FIG. 4 and illustrates an alternative embodiment of the flange structure in which the load flanks of the inner and outer flanges are orientated in an outwardly diverging relationship to locate an area of engagement of the load flanks radially inward near a root region of the inner flange.
Figure 9:
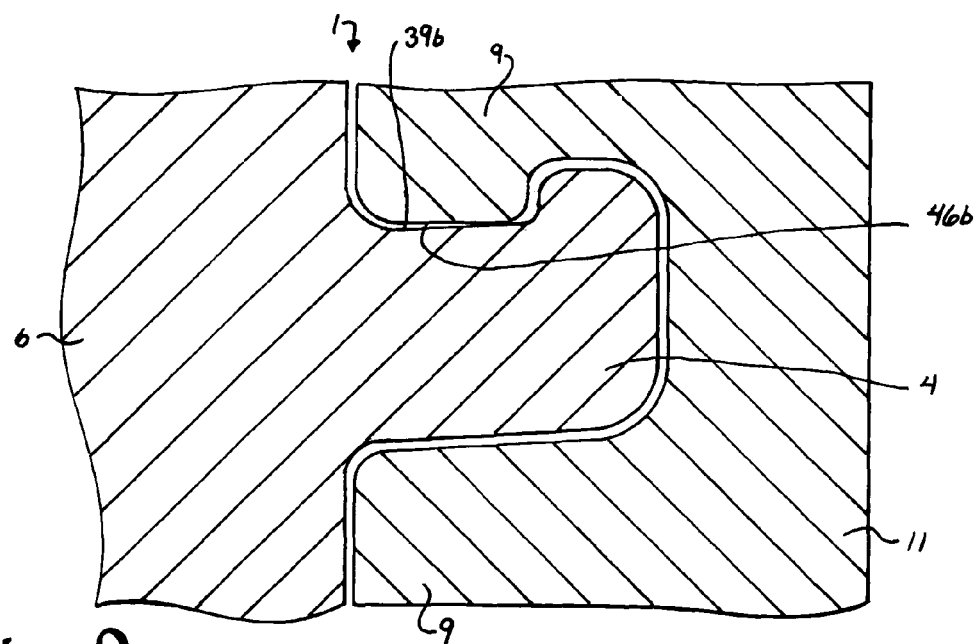
FIG. 9 is a view similar to FIG. 4 and illustrates an alternative embodiment of the flange structure in which the load flanks of the inner and outer flanges are orientated in an outwardly converging relationship to locate an area of engagement of the load flanks radially outward near a crest region of the inner flange.

FIGS. 8 and 9 illustrate variations in the guide and advancement flange structure 1 in which the load flanks 39 and 46 are non-parallel. Proportioning of the axial stresses between the inner flange 4 and the outer flange 9 can be controlled, to some extent, by controlling the location of engagement between the flanges 4 and 9. FIG. 8 shows the flange structure 1 with load flanks 39a and 46a diverging in a radially outward direction. Such a relative orientation moves the location of contact between the load flanks 39a and 46a radially inward, as compared to a flange structure 1 with parallel load flanks 39 and 46. The result of this variation is that the effective local moment arm of stress between the flanges 4 and 9 is shortened for the inner flange 4 and lengthened for the outer flange 9. The outwardly diverging load flanks 39a and 46a, thus, increase the proportion of axial stress that is applied to the outer flange 9 where it is connected to the outer member 11. In contrast, FIG. 9 shows a configuration of the flange structure 1 in which the load flanks 39b and 46b converge in an outward radial direction. Outward convergence of the load flanks 39b and 46b moves the location of axial engagement between the flanges 4 and 9 outward, as compared to parallel load flanks 39 and 46, thereby increasing the effective local moment arm of axial stress on the inner flange 4 and decreasing it for the outer flange 9. The capability of controlling the proportioning of axial stress on the flanges 4 and 9 gives the flange designer control of which flange is more likely to fail in a situation of extreme torque between the inner and outer members 6 and 11.

Figure 10:
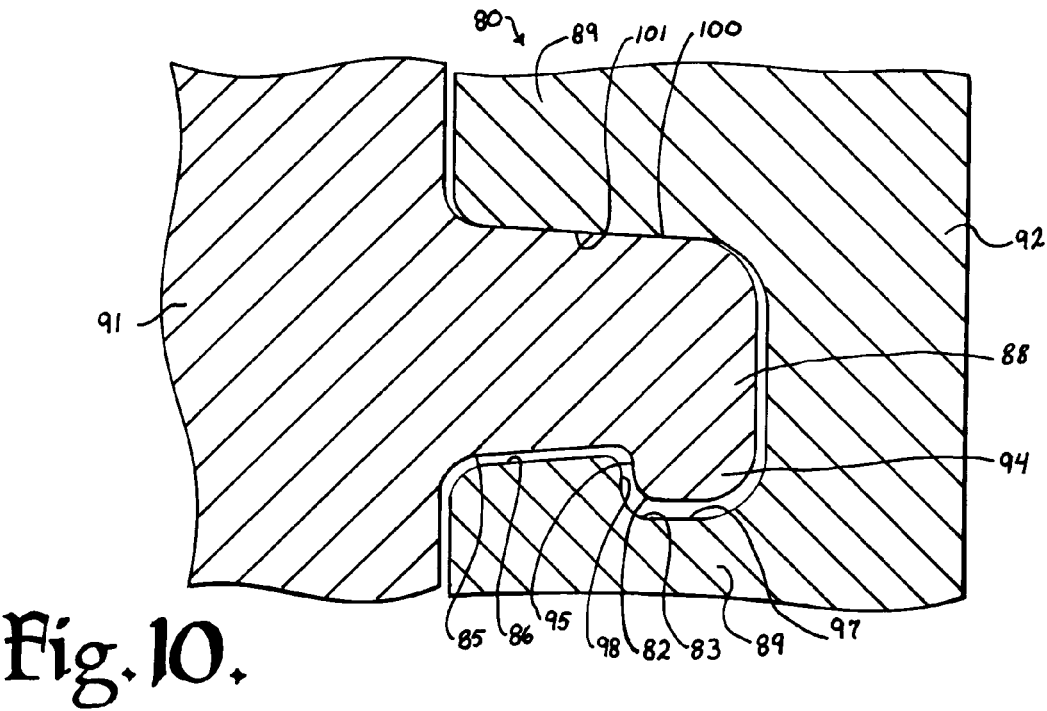
FIG. 10 is a further enlarged fragmentary sectional view illustrating an alternative embodiment of the flange structure of the present invention with an anti-splay lip on a stab flank of an inner flange and an anti-splay groove on a stab flank of an outer flange, the load flanks being parallel and somewhat positive in angular orientation relative to the helical axis.
Figure 11:
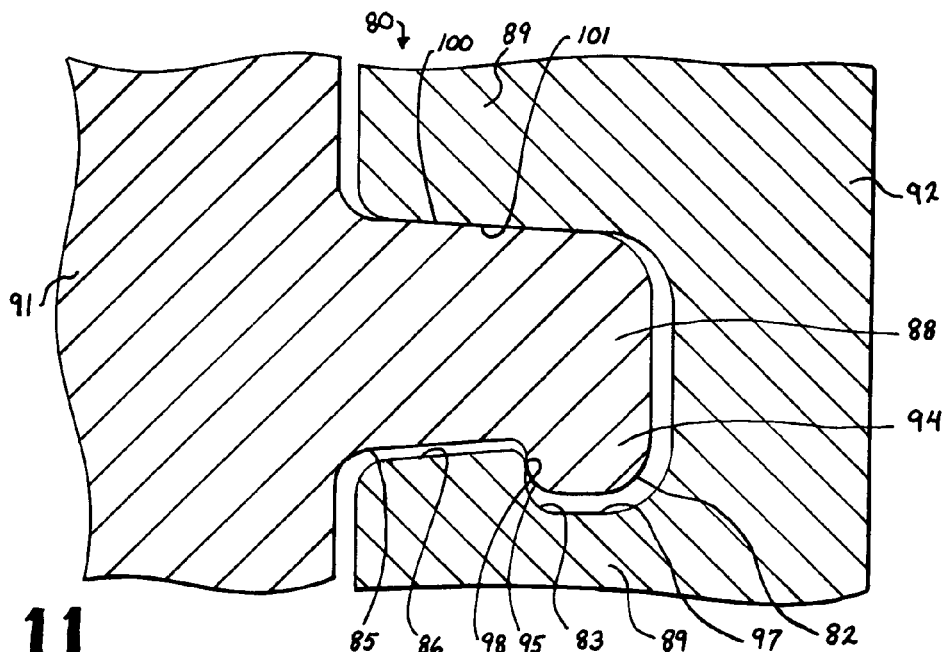
FIG. 11 is a view similar to FIG. 10 and illustrates the flange structure with the inner member strongly torqued within the outer member, thereby mutually engaging the anti-splay surfaces of the lip and groove.

FIGS. 10-15 illustrate modified embodiments of an anti-splay helical guide and advancement flange structure 80 in which anti-splay contours 82 and 83 are formed on stab flanks 85 and 86 of an inner flange 88 and an outer flange 89 respectively of an inner member 91 and an outer member 92. The illustrated anti-splay contour 82 of the inner flange 88 forms a lip 94 including an anti-splay shoulder 95. Similarly, the anti-splay contour 83 of the outer flange 89 forms a groove 97 including an anti-splay shoulder 98. Radial engagement of the shoulders 95 and 98 limits splaying of the outer member 92 when the inner member 91 is strongly torqued therein, as shown in FIG. 11.

Figure 12:
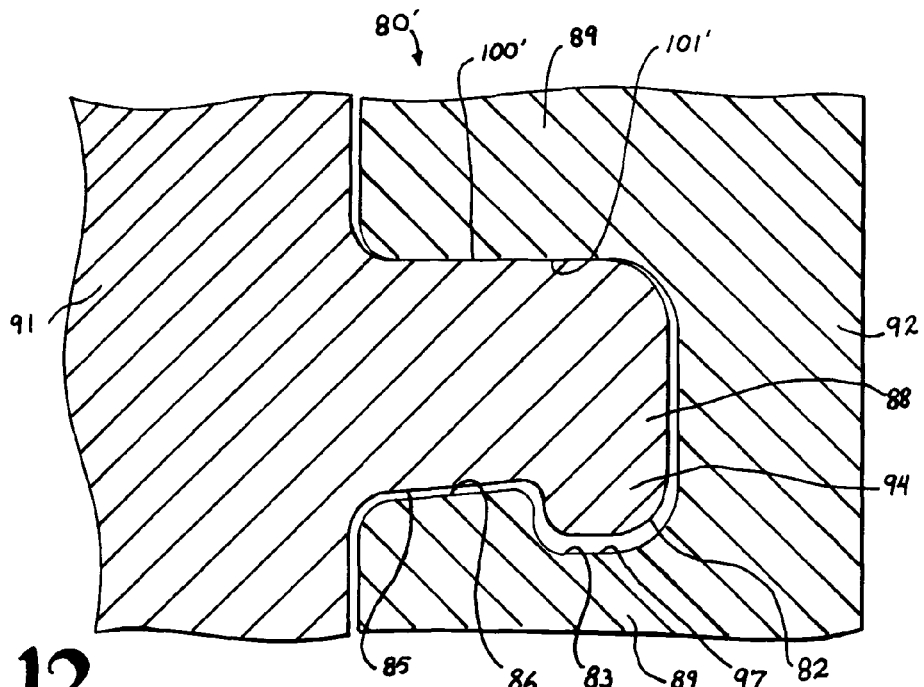
FIG. 12 is a view similar to FIG. 10 and illustrates an alternative embodiment of the flange structure with the load flanks parallel and substantially perpendicular to the helical axis.
Figure 13:
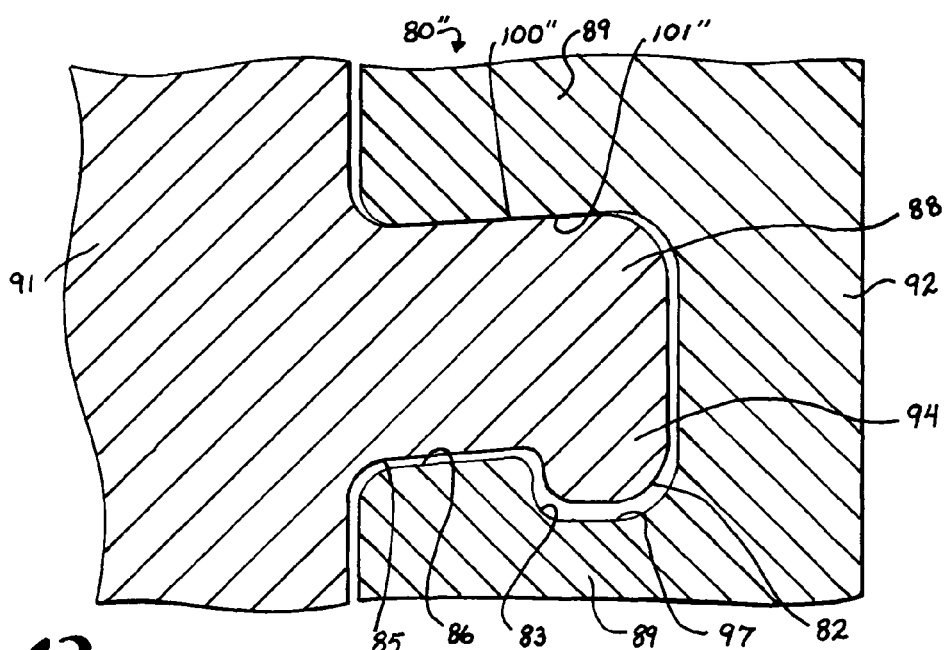
FIG. 13 is a view similar to FIG. 10 and illustrates an alternative embodiment of the flange structure with the load flanks parallel and somewhat negative in angular orientation to the helical axis.
Figure 14:
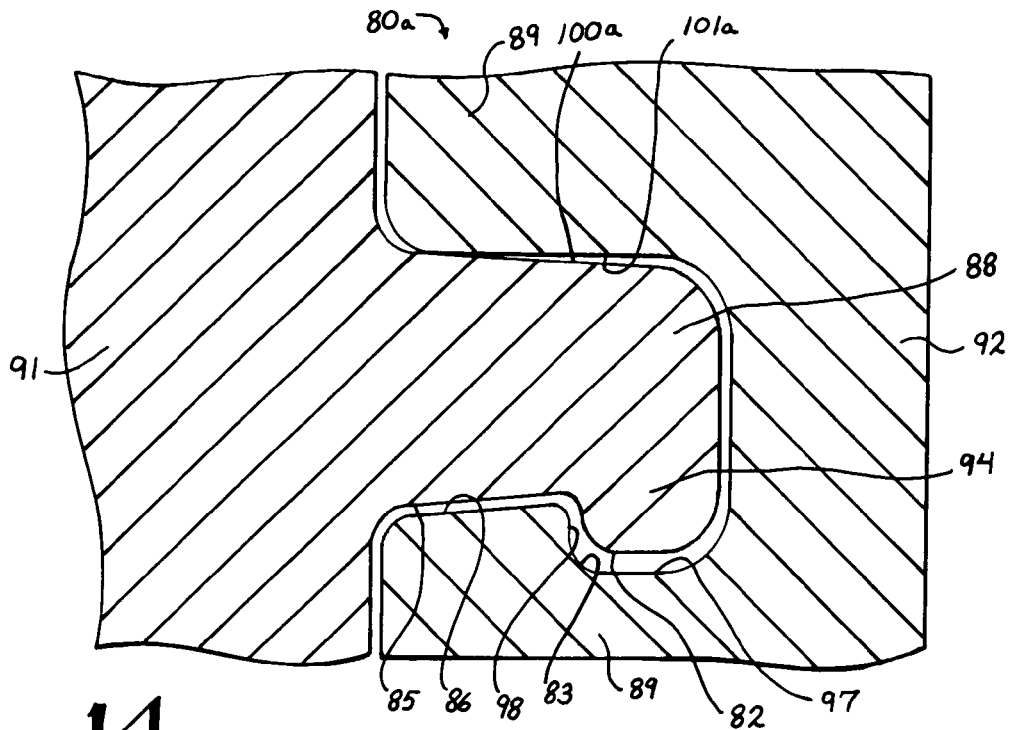
FIG. 14 is a view similar to FIG. 10 and illustrates an alternative embodiment of the flange structure in which the load flanks of the inner and outer flanges are orientated in an outwardly diverging relationship to locate an area of engagement of the load flanks radially inward near a root region of the inner flange.
Figure 15:
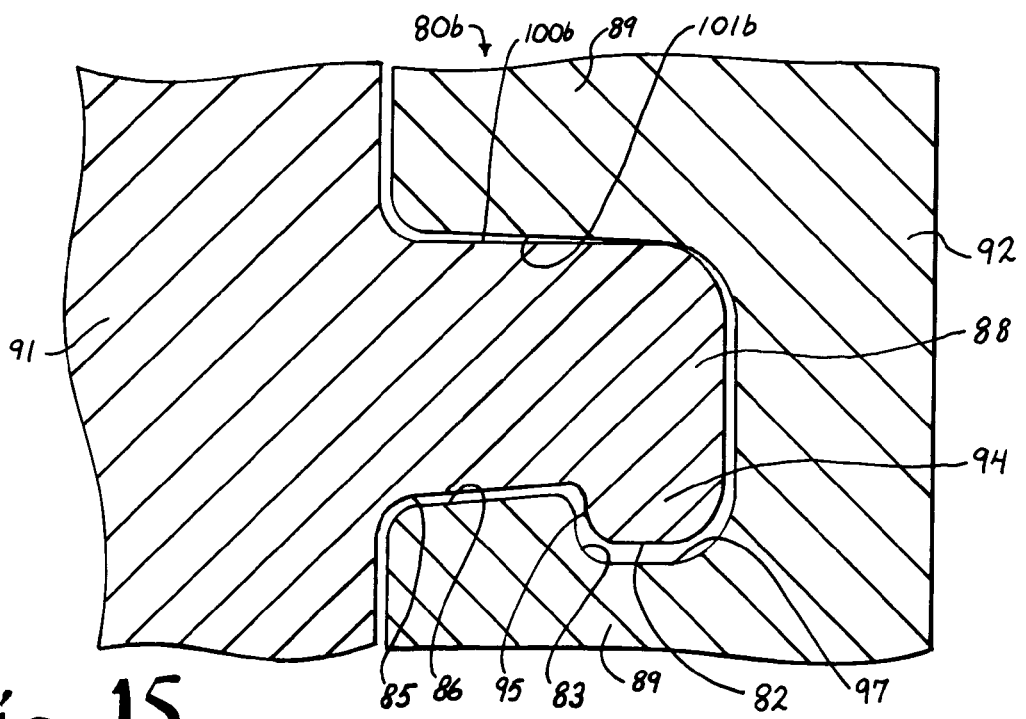
FIG. 15 is a view similar to FIG. 10 and illustrates an alternative embodiment of the flange structure in which the load flanks of the inner and outer flanges are orientated in an outwardly converging relationship to locate an area of engagement of the load flanks radially outward near a crest region of the inner flange.

Referring to FIGS. 10 and 11, the inner flange 88 includes a load flank 100, while the outer flange 89 has a load flank 101. The load flanks 100 and 101 are mutually parallel and oriented at a slightly positive or obtuse angle relative to a helical axis analogous to the helical axis 41 of FIG. 3. FIG. 12 illustrates a flange structure 80', similar to the flange structure 80, in which load flanks 100' and 101' are mutually parallel and oriented perpendicular to the helical axis of the structure 80'. In FIG. 13, a flange structure 80" is illustrated in which load flanks 100" and 101" are mutually parallel and oriented at a slight negative angle relative to the helical axis of the flange structure 80". FIGS. 14 and 15 illustrate variations of the flange structure 80 with anti-splay contours 82 and 83 on the respective stab flanks 85 and 86 in which the load flanks 100 and 101 are non-parallel. In the flange structure 80a, shown in FIG. 14, load flanks 100a and 101a diverge in a radially outward direction. In FIG. 15, a flange structure 80b is shown in which load flanks 100b and 101b converge in a radially outward direction.

Figure 16:
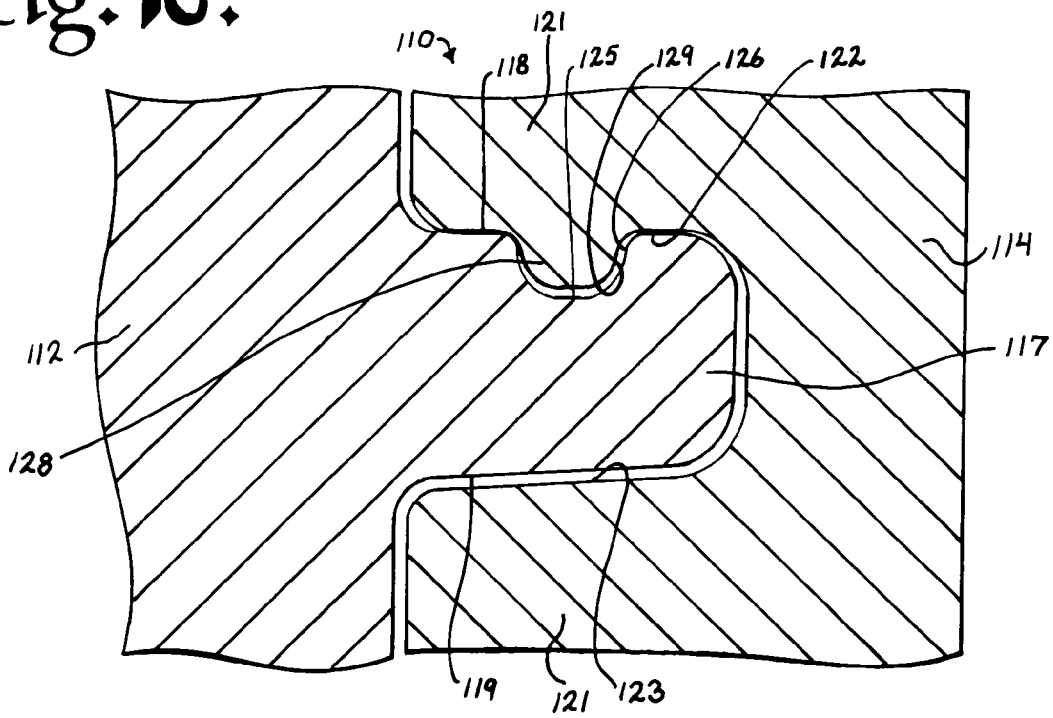
FIG. 16 is a further enlarged fragmentary sectional view illustrating an alternative embodiment of the flange structure of the present invention with an anti-splay lip on a load flank of an outer flange and an anti-splay groove on a load flank of an inner flange, the lip and groove being positioned at radial location intermediate the root and crest regions of the flanges.
Figure 17:
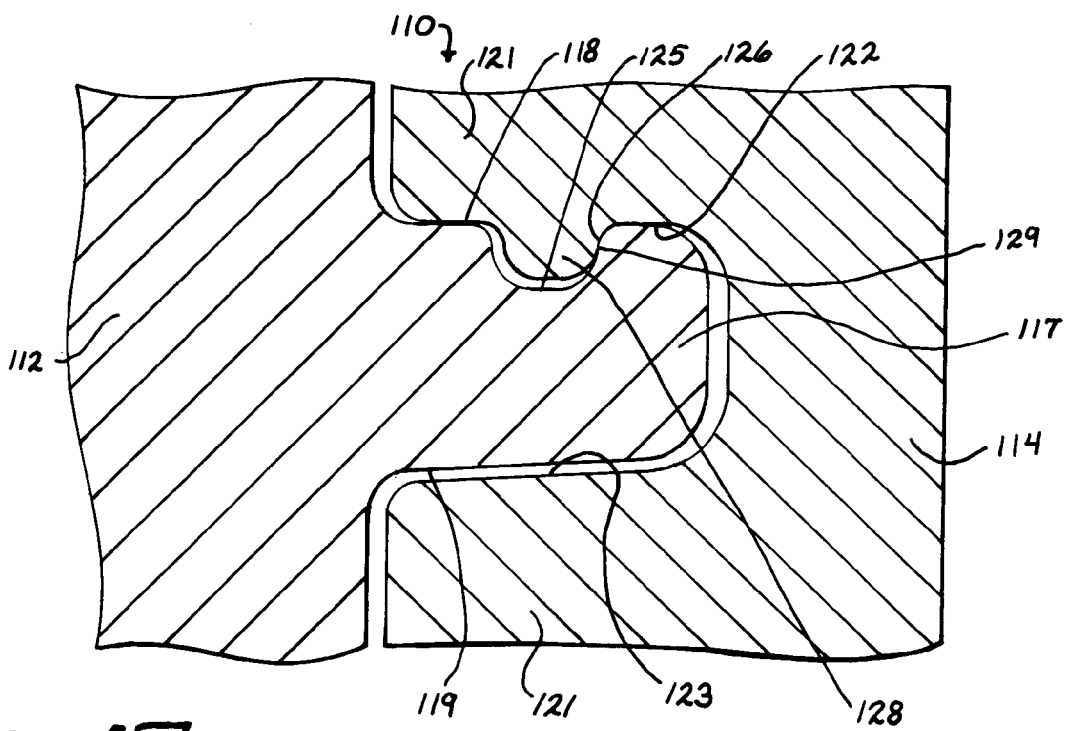
FIG. 17 is a view similar to FIG. 16 and illustrates the flange structure with the inner member strongly torqued within the outer member, thereby mutually engaging the anti-splay surfaces of the lip and groove.

In the flange structures 1 and 80 and variations thereof, the anti-splay lip and groove are positioned at the inner or outer extremes of the flanges. However, it is foreseen that the lip and groove could also be positioned at any radial position on the flanges. FIGS. 16 and 17 illustrate a configuration of an anti-splay helical guide and advancement flange structure 110 formed on an inner member 112 and an outer member 114. The inner member 112 has an inner flange 117 with a load flank 118 and an opposite stab flank 119. Similarly, the outer member 114 has an outer flange 121 with a load flank 122 and a stab flank 123. The inner flange 117 has an anti-splay contour on the load flank 118 forming an anti-splay groove 125 including an anti-splay shoulder 126. The groove is positioned radially between inner and outer extremes of the inner flange 117. The illustrated outer flange 121 has an anti-splay contour on the load flank 122 forming an anti-splay lip 128 including an anti-splay shoulder 129. The lip 128 is positioned radially to align with the groove 125 when the inner member 112 is advanced into the outer member 114. The groove 117 and lip 128 could alternatively be formed on the stab flanks 119 and 123. Additionally, the groove 117 could alternatively be formed on the outer flange 121 with the lip 128 on the inner flange 117. Finally, the load flanks 118 and 122 could alternatively be angled positively or negatively or be formed in diverging or converging relation within the present invention.

Figure 18:
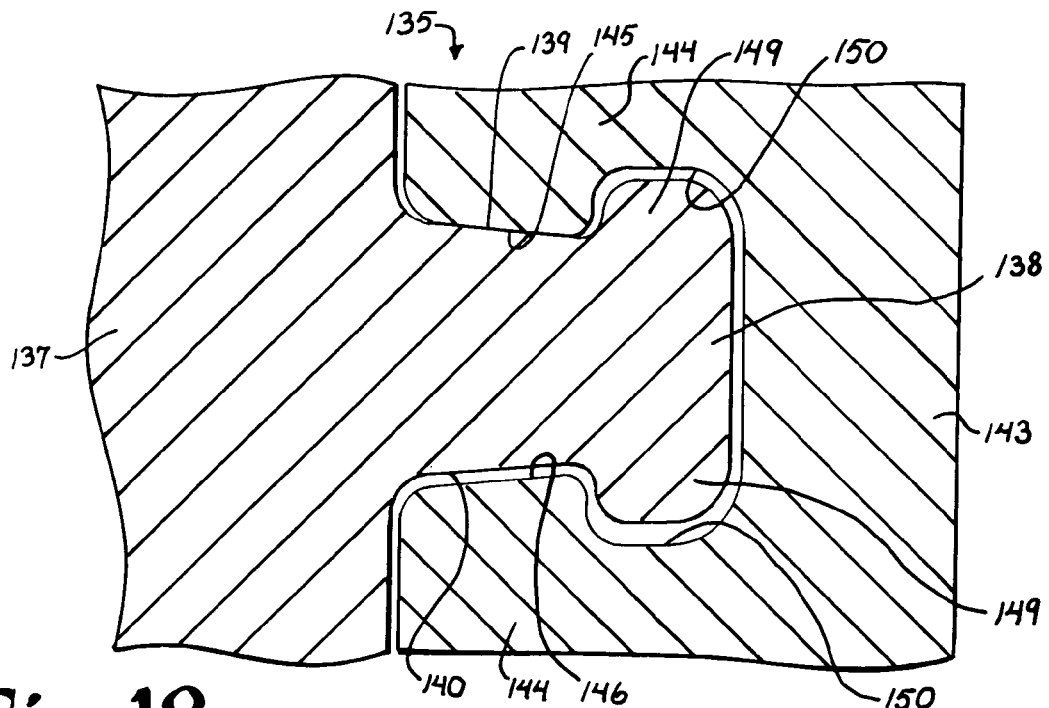
FIG. 18 is a further enlarged fragmentary sectional view illustrating an alternative embodiment of the flange structure of the present invention with an anti-splay lip on both the load flank and the stab flank of an inner flange and an anti-splay groove on both load flank and a stab flank of an outer flange.
Figure 19:
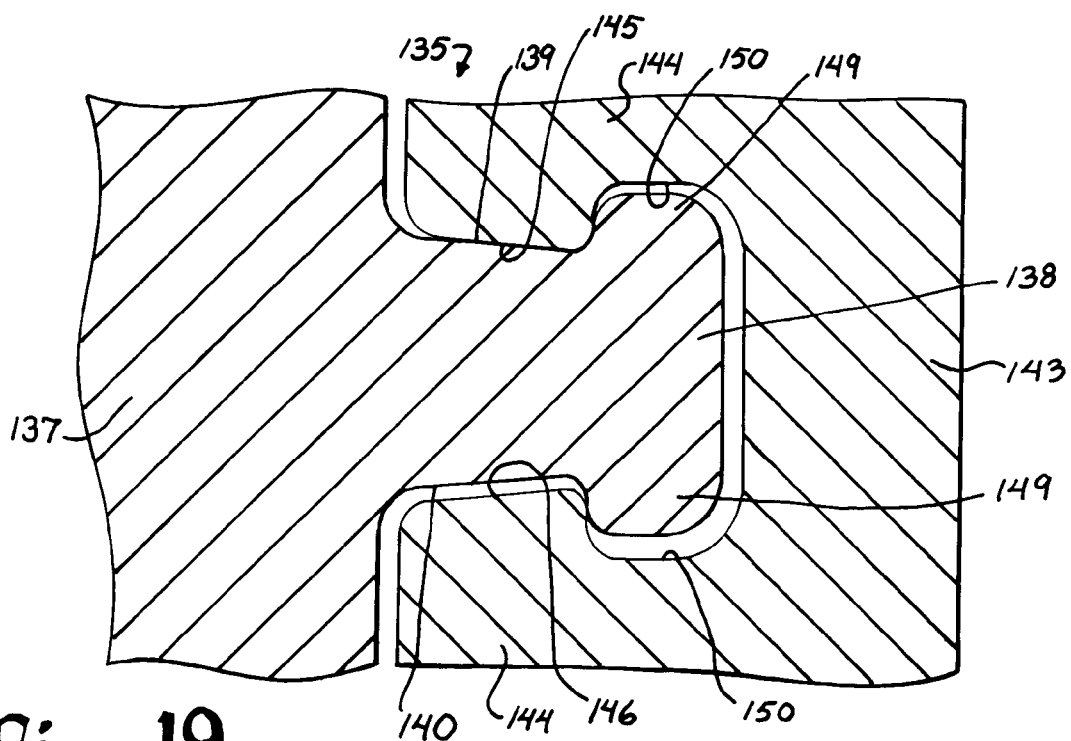
FIG. 19 is a view similar to FIG. 18 and illustrates the flange structure with the inner member strongly torqued within the outer member, thereby mutually engaging the anti-splay surfaces of the lips and grooves.

FIGS. 18 and 19 illustrate a modified embodiment of an anti-splay helical guide and advancement flange structure 135 in which anti-splay contours are formed on both load flanks and stab flanks of the flanges. An inner member 137 has an inner flange 138 with a load flank 139 and a stab flank 140. Similarly, an outer member 143 has an outer flange 144 with a load flank 145 and a stab flank 146. An anti-splay lip 149 is formed on both the load flank the load flank 139 and the stab flank 140 of the illustrated inner flange 138. A complementary anti-splay groove 150 is formed on both the load flank 145 and the stab flank 146 of the outer flange 144. Radial engagement of the lips 149 with the grooves 150 limits splaying of the outer member 143 when the inner member 137 is strongly torqued therein. The load flanks 139 and 145 of the flange structure 135 could alternatively be angled neutrally or negatively or diverging or converging.

Figure 20:
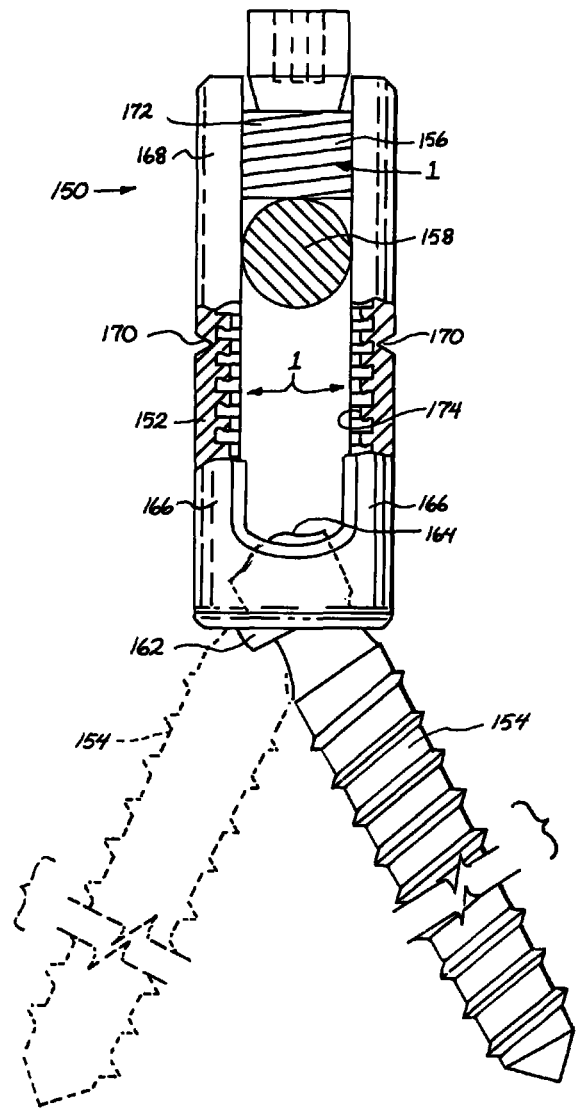
FIG. 20 is an enlarged fragmentary side elevational view of a spinal implant incorporating the helical guide and advancement flange with a radially loaded lip which embodies the present invention and including a polyaxial bone screw.

FIG. 20 illustrates a polyaxial medical implant 150 which incorporates the helical guide and advancement flange structure 1 of the present invention. The illustrated polyaxial implant 150 includes an open headed receiver 152, a threaded shank 154, and a closure 156 which cooperate to fix the position of another implant member, such as a spinal fixation rod 158. The receiver or head 152 is configured internally with a spherical socket (not shown) which receives a shank retainer member 162 having a spherical outer surface. The retainer member 162 is connected to a capture end 164 of the shank 154 and, in cooperation with the receiver socket, enables the shank 154 to be positioned at any desired angle relative to the receiver 152, within a conical range of movement. The shank 154 is secured at the desired angle by engagement of the rod 158 with the capture end 164 when the rod is clamped within the receiver 152 by the closure 156. Additional information about polyaxial bone screws can be found in U.S. Pat. No. 6,716,214 which is incorporated herein by reference.

The receiver 152 includes spaced apart arms 166 and preferably includes break-off extensions 168 which are separable from the arms 166 by breaking the extensions 168 off at weakened regions 170. The flange structure 1 includes an anti-splay closure guide and advancement flange 172 formed on the closure 156 which cooperates with a discontinuous receiver anti-splay guide and advancement flange 174 formed on inner surfaces of the arms 166 and extensions 168. The flanges 172 and 174 are substantially similar to the flanges 4 and 9 of the implant 3 and benefit from the same variations in configuration as described in connection therewith. The flanges 172 and 174 enable the closure 156 to be advanced into clamping contact with the rod 158 by rotation within the receiver 152. In other respects, the implant 150 is substantially similar to the implant 3.

It is to be understood that while certain forms of the present invention have been illustrated and described herein, it is not to be limited to the specific forms or arrangement of parts described and shown.

What is claimed and desired to be secured by Letters Patent is as follows:

1. A flange structure for guiding and advancing an inner member into an outer member having spaced arms along an axis in response to relative rotation between said inner member and said outer member about said axis and comprising:
   (a) an inner flange helically wound about and along said inner member;
   (b) a discontinuous outer flange helically wound about and along an opening in said outer member;
   (c) one of said inner and outer flanges being a lipped flange and having a lip projecting axially therefrom and extending therealong, said lip having an axial peak and a curvate surface;
   (d) the other of said flanges being a grooved flange and having a groove formed axially into said grooved flange and extending therealong, said groove having an axial trough and a curvate surface; and
   (e) said lipped flange and said grooved flange being configured in such a manner so as to radially interlock to resist radial splaying of the outer member arms relative to the inner member and so as to enable rotary joining of portions of said lip and said groove in response to said inner member being rotated relative to said outer member and being helically advanced into said outer member.

2. A structure as set forth in claim 1 wherein:
   (a) said arms including main portions and extended portions connected to said main portions by weakened regions, said outer flange extending longitudinally along said arm inner surfaces.

* * * * *

UNITED STATES PATENT AND TRADEMARK OFFICE
CERTIFICATE OF CORRECTION

PATENT NO. : 8,876,868 B2
APPLICATION NO. : 11/101859
DATED : November 4, 2014
INVENTOR(S) : Roger P. Jackson It is certified that error appears in the above-identified patent and that said Letters Patent is hereby corrected as shown below:

In the Claims

- Claim 2, Column 14, Line 31, delete "said arm".

- Claim 2, Column 14, Line 31, insert --of said arms-- following 'surfaces'.

Signed and Sealed this
Sixteenth Day of August, 2022

*Katherine Kelly Vidal*

Katherine Kelly Vidal
*Director of the United States Patent and Trademark Office*